United States Patent [19]
Steffan

[11] Patent Number: 5,512,479
[45] Date of Patent: Apr. 30, 1996

[54] METHOD OF DEGRADING VOLATILE ORGANOCHLORIDES AND REMEDIATION THEREOF

[75] Inventor: Robert J. Steffan, Newtown, Pa.

[73] Assignee: Envirogen, Inc., Lawrenceville, N.J.

[21] Appl. No.: 136,792

[22] Filed: Oct. 14, 1993

[51] Int. Cl.$^6$ .............................. B09C 1/10; C12N 9/02; C12N 1/38

[52] U.S. Cl. .................. 435/262.5; 435/189; 435/253.3; 210/601

[58] Field of Search ..................................... 435/262, 189, 435/262.5, 253.3, 874; 210/601

[56] References Cited

U.S. PATENT DOCUMENTS

| | | | |
|---|---|---|---|
| 4,853,334 | 8/1989 | Van den Bergh et al. | 435/262 |
| 5,024,949 | 6/1991 | Hegeman et al. | 435/262 |
| 5,079,166 | 1/1992 | Winter et al. | 435/262 |
| 5,171,684 | 12/1992 | Yen et al. | 435/252.3 |

OTHER PUBLICATIONS

Yen, Kwang-Yu, "Cloning and Characterization of a *Pseudomanas mendocina* KR1 Gene Cluster Encoding Toluene–4–Monooxygenase," *Journal of Bacteriology*, vol. 173, No. 17, Sep. 1991, pp. 5315–5327.

Shields, Malcolm S. and Reagin, Michael R., "Selection of a *Pseudomonas cepacia* Strain Constitutive for the Degradation of Trichloroethylene," *Applied and Environmental Microbiology*, vol. 58, No. 12, Dec. 1992, pp. 3977–3983.

Whited, Gregory M. and Gibson, David T., "Toluene–4–Monooxygenase, a Three–Component Enzyme System that Catalyzes the Oxidation of Toluene to p–Cresol in *Pseudomonas mendocina* KR1", *Journal of Bacteriology*, vol. 173, No. 9, May 1991, pp. 3010–3016.

Nelson, Michael J. K., Montogomery, Stacy O., and Pritchard, P. H., "Trichloroethylene Metabolism by Microorganisms that Degrade Aromatic Compounds", *Applied and Environmental Microbiology*, vol. 54, No. 2, Feb. 1988, pp. 604–606.

Primary Examiner—Donald E. Czaja
Assistant Examiner—T. J. Reardon
Attorney, Agent, or Firm—Miller & Christenbury

[57] ABSTRACT

A process for degrading volatile organic contaminants such as trichloroethylene. and remediating volatile organic contaminant contaminated media using trichloroethylene induced toluene monooxygenase activity in *Pseudomonas mendocina* KR-1 is described.

21 Claims, 7 Drawing Sheets

METHOD OF DEGRADING VOLATILE ORGANOCHLORIDES AND REMEDIATION THEREOF

FIELD OF THE INVENTION

The present invention relates to a method of degrading volatile organochlorides, particularly to a method of degrading volatile organochlorides such as trichloroethylene using trichloroethylene to induce toluene monooxygenase gene activity in *Pseudomonas mendocina* KR-1.

BACKGROUND OF THE INVENTION

Volatile organochlorides (VOC's) are common environmental pollutants known for their toxicity and the hazards presented when in contact with humans. VOC's include trichloroethylene, dichloroethylene, vinyl chloride, ethylene chloride and the like. Trichloroethylene (TCE) is an especially well known VOC, used for a variety of purposes such as for solvent extraction, as a degreaser in dry cleaning and the manufacture of organic chemicals, pharmaceuticals and the like. Leaky above or below underground storage tanks, spills or improper disposal of waste materials containing VOC's such as TCE can pollute aquifers, soils, ground water, waste water and the like.

A number of techniques have been developed to degrade or remove TCE and related VOC's under a number of conditions. However, they are typically quite limited in their flexibility of use and have proven to be less than effective. Many of these efforts have concentrated in the microbial degradation of TCE and VOC's. However, the efforts to date have fallen short of the desire to cost effectively and completely remediate soils and/or contaminated ground water and/or waste materials.

To date, most biological systems for degrading TCE require the use of specialized microorganisms and/or the induction of specialized genes. Gene induction is the process by which genes are activated and remain in an activated mode. Gene induction typically requires the presence of an inducing co-substrate, many of which are toxic, hazardous substances.

For example, Shields et al in "Selection of a *Pseudomonas cepacia* Strain Constitutive for the Degradation of Trichloroethylene", Applied and Environmental Microbiology, Vol. 58, p. 3977–3983 (December 1992), employs recombinant *Pseudomonas cepacia* in an attempt to degrade TCE, toluene, phenol or m-trifluoromethyl phenol. *Pseudomonas cepacia* G4 was unable to degrade TCE when grown without an inducer. *Pseudomonas cepacia* 5223-PR1, did display the ability to degrade TCE. However, the possible successful degradation of TCE in Shields et al relies on recombinant microorganisms.

Nelson et al in "Trichloroethylene Metabolism by Microorganisms That Degrade Aromatic Compounds", Applied and Environmental Microbiology, Vol. 54, pg. 604–606, (February 1988), tested six strains known for degrading naphthalene, biphenyl and toluene for potential ability to degrade TCE. *Pseudomonas putida* PpF1 and *Pseudomonas putida* B5 demonstrated some ability to degrade TCE. However, successful TCE degradation occurred only upon induction by addition of toluene or phenol. Of course, it is critically disadvantageous in remediating contaminated soils, ground water and waste materials when induction or degradation requires addition of further toxic substances to the media subjected to the remediation treatment.

Whited et al in "Toluene-4-Monooxygenase, a Three-Component Enzyme System That Catalyzes the Oxidation of Toluene to p-Cresol in *Pseudomonas mendocina* KR1", Journal of Bacteriology, Vol. 179, p.3010–3016, (May 1991), discloses oxidation of toluene to p-cresol, the degradation being initiated by toluene-4-monooxygenase enzyme. No ability to degrade TCE was tested or found.

Subsequent to Whited et al, Yen et al in "Cloning and Characterization of a *Pseudomonas mendocina* KR1 Gene Cluster Encoding Toluene-4-Monooxygenase", Journal of Bacteriology, Vol. 173, p. 5315–5327 (September 1991), further investigated the toluene-4-monooxygenase pathway for hydroxylation of toluene to p-cresol. Although they acknowledge the importance of T4MO in the degradation of trichloroethylene, they did not perform any testing in this regard. Moreover, they employed recombinant *Escherichia coli*.

U.S. Pat. No. 5,079,166 discloses a method of microbial degradation of trichloroethylene employing *Pseudomonas mendocina* KR-1. However, '166 employs recombinant cells treated with an inducer of toluene monooxygenase (TMO) genes. '166 further discloses the degradation of TCE with recombinant *Pseudomonas putida* Y2101 cells. The recombinant Y2101 cells are also treated with an inducer of TMO. Certain of the cell lines from *Pseudomonas mendocina* KR-1 employ particular inducers. For example, pKY277, pKY280, pKY281 and pKY282 employ toluene as an inducer. Similarly, pMY402, pMY405, pMY401 and pMY404 employ isopropyl-β-D-thiogalactopyranoside. pKY287 employs a change in temperature as the inducer. Of course, '166 has the disadvantage in the remediation context of utilizing recombinant organisms and requiring an inducer to initiate degradation.

Winter et al, "Efficient Degradation of Trichloroethylene By a Recombinant *Escherichia coli*" (*Bio/Technology*, pp 282–285, March 1989), discloses much of the subject matter as the '166 patent, including duplicative cell lines.

All of the above examples have the disadvantages of either not working to successfully degrade VOC's, require toxic or additional inducer substrates to achieve degradation of VOC, or rely on recombinant cell lines.

Many VOC's, especially TCE and its toxic properties, make it imperative that the contaminant be promptly, efficiently and effectively removed from locations where contact with humans is possible. Many constraints, however, frequently inhibit or prevent removal of the offending TCE. For example, in many instances the contaminant has progressed downwardly into the ground to a point where excavation is impossible or impractical. The soil must therefore be decontaminated in situ. This critical common restriction eliminates the potential use of many possible decontamination technologies, such as those described above. Many alternative technologies have been attempted in efforts to effectively and efficiently decontaminate TCE polluted areas. However, these technologies have proven inadequate in achieving complete remediation or are environmentally incompatible, practically not viable or cost prohibitive. For example, a number of technologies treat groundwater or soil, but not both, which is highly desirable to achieve complete remediation in many cases. Similarly, the need for toxic inducers in several technologies is quite impractical.

OBJECTS OF THE INVENTION

It is an object of the present invention to provide a method of degrading VOC's such as TCE and alkanes as a means of remediating soils, ground water, waste waters, waste materials, aquifers and the like.

It is another aspect of the invention to provide a method of degrading VOC's such as TCE without the need for additional toxic substrates to complete the process.

It is a further object of the present invention to provide a method of degrading VOC's such as TCE that employs natural microorganisms and does not require additional inducers to initiate the degradation process.

Other objects and advantages of the present invention will become apparent to those skilled in the art from the drawings, the detailed description of preferred embodiments, and the appended claims.

SUMMARY OF THE INVENTION

The present invention provides a novel process for degrading VOC's such as trichloroethylene. In one of its aspects the process includes degrading VOC's by contacting naturally occurring *Pseudomonas mendocina* KR-1 with trichloroethylene or alkanes. Degradation of the VOC's is catalyzed by induction of toluene monooxygenase genes naturally occurring within the *Pseudomonas mendocina* KR-1.

In another of its aspects, the present invention provides a novel process for remediating a medium contaminated with one or more VOC's. The process includes treating the medium containing the VOC's with Pseudomonas mendocina KR-1. The material to be remediated can include any number of ground water, waste water, soil and sludges, sediments, drinking water, leachates, chemical waste and the like.

DETAILED DESCRIPTION OF THE INVENTION

It will be appreciated that the following description is intended to refer to the specific embodiments of the invention selected for illustration in the graphs shown in the drawings and is not intended to define or to limit the invention other than in the appended claims.

The present invention provides a novel method of degrading VOC's, with particular emphasis on trichloroethylene, and a novel method of remediating a wide variety of materials containing trichloroethylene. It has been unexpectedly discovered that naturally occurring *Pseudomonas mendocina* KR-1, without the need of additional co-substrates for TMO induction, degrades trichloroethylene contained within a medium upon treating the trichloroethylene or upon contacting the trichloroethylene with the *Pseudomonas mendocina* KR-1. This surprising result is achieved without the necessity of employing recombinant cell lines as has been the case in the past. The examples listed below and the graphs shown in the drawings indicate the ability of *Pseudomonas mendocina* KR-1 to increase TMO activity without the need for extraneous inducers and cause the subsequent degradation of TCE.

*Pseudomonas mendocina* KR-1 has been deposited with the American Type Culture Collection (ATCC) of 12301 Parklawn Drive, Rockville, Md. 20852, under ATCC Accession No. 55706. The Deposit was made on Sep. 1, 1995.

TMO has been known to catalyze the destruction of TCE. Prior technology which utilized TMO for TCE degradation, however, relied on the presence of toxic co-substrates such as toluene or phenol to stimulate the induction of the TMO genes, or the use of genetic engineering to de-regulate TMO production. This has severe disadvantages in attempting to remediate contaminated media. Introduction of toluene or phenol, in addition to TCE already contaminating the media, is simply environmentally impractical. Similarly, recombinant cells also require toxic co-substrates or other artificial catalysts to induce TMO activity. In addition, cost considerations associated with such cells are prohibitive. Likewise, the in situ application of TMO-producing bacteria for the remediation of TCE contamination (e.g. contaminated aquifers, etc.) has been limited by the need to stimulate TMO induction by the addition of inducing co-substrates. The discovery of TCE induced TMO activity creates the possibility for alternative environmentally safe treatment strategies that do not rely on the presence of toxic co-substrates or other additional catalysts.

A series of two experiments containing two runs each were performed to test the ability of TCE to cause induction of TMO genes naturally occurring in *P. mendocina* KR-1.

EXAMPLES 1(a) AND 1(b)

Cells were first grown overnight under non-inducing conditions. Specifically, cells were grown by suspending a small amount of cells from agar plate, or broth media, in a 125 mL flask containing 50 mL of basal salts medium (BSM) containing 3 g/L sodium glutamate with or without 0.1 g/L casamino acids (Difco). Cells were placed on a rotary shaker and shaken at 100 rpm and 30° C. for 16–24 hr. The cells were then centrifuged and washed with BSM. They were subsequently suspended in BSM and glutamate (3 g/L) to an optical density at 550 nm ($OD_{550}$) of 1.0. Ten mL of cell suspension was added to a 50 mL serum vial, and 10 μL TCE (40 mM) dissolved in dimethylformamide (DMF) was added to a final concentration of 40 μM.

EXAMPLES 1(c) AND (d)

Comparison non-induced samples were prepared by adding only dimethylformamide (10 μL) to replicate 10 mL cell suspensions. The comparison samples contained no TCE. All sample vials were sealed with teflon-coated crimp seals and the cell suspensions were shaken at 25° C. TMO activity was determined at timed intervals by using a $^{14}$C-toluene assay that measured the conversion of radioactive toluene to non-volatile products.

The $^{14}$C toluene assay was performed by adding 0.5 mL of cells at an optical density at 550 nm ($OD_{550}$) of 0.5 to a small glass test tube. 5 µL of $^{14}$C toluene (0.033 to 0.1 µCi/µL was added to the cells, they were mixed on a vortex mixer, and incubated for 5 minutes at room temperature. Then, 20 µl of the mixture was removed and spread evenly onto a 1.5×2.0 cm piece of silica gel-coated polyester thin layer chromatography plate (Whatman Ltd; PE SIL G/UV, cat. no. 4410 222). Air was passed over the silica gel for 20 minutes to dry the gel and remove residual $^{14}$C toluene. The silica gel piece was then placed into a liquid scintillation vial containing 5.0 mL of OptiPhase "HiSafe" 3 liquid scintillation cocktail (LKB Scintillation Products). Radioactivity in the bottles was enumerated by placing the bottles in a liquid scintillation counter. Results were recorded as disintegrations per minute (DPM). TMO activity was relative to the amount of $^{14}$C toluene converted to non-volatile products during the 5 minute incubation. Non-volatile products were not evaporated from the silica gel during the drying phase, and were enumerated by scintillation counting. Thus, the greater the DPMs, the greater the TMO activity.

Figure 1:
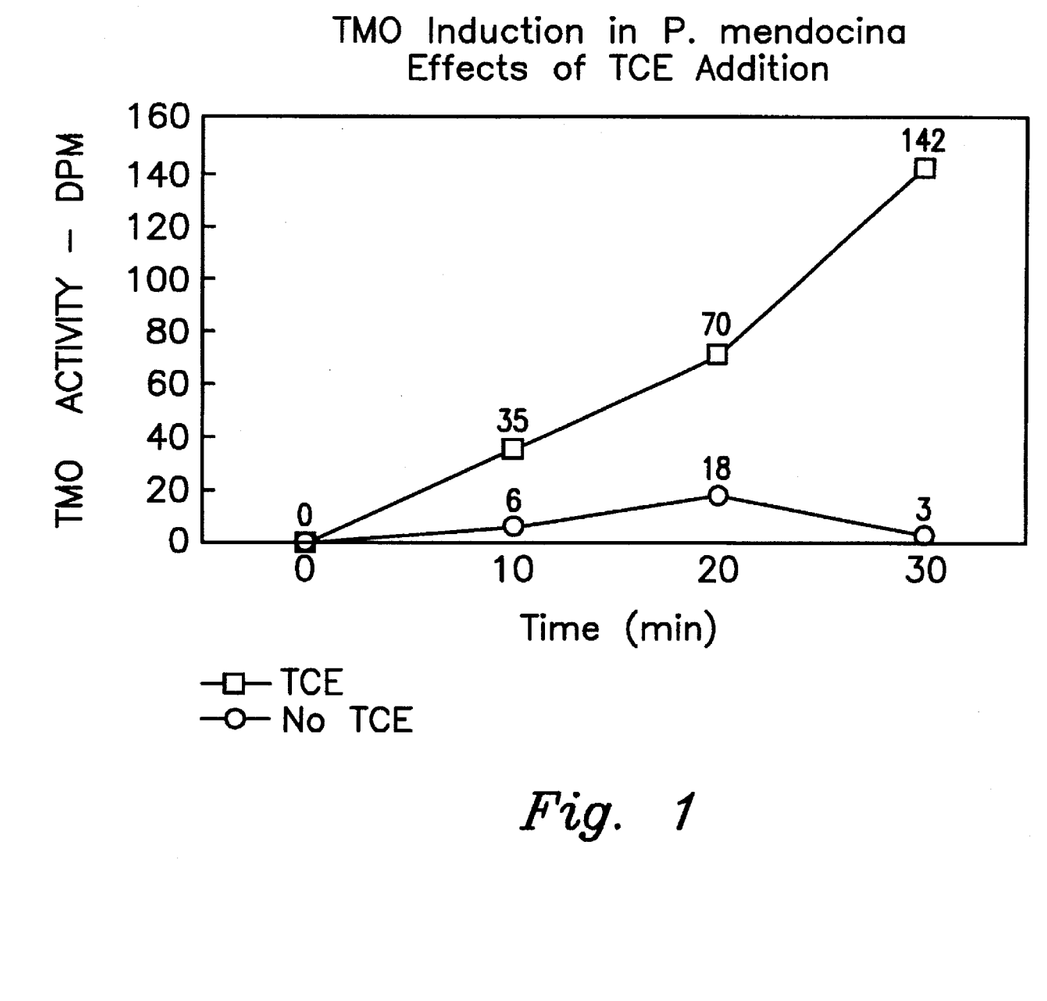
FIG. 1 is a graph of TMO activity in *Pseudomonas mendocina* over 30 minutes time, with and without trichloroethylene.
Figure 2:
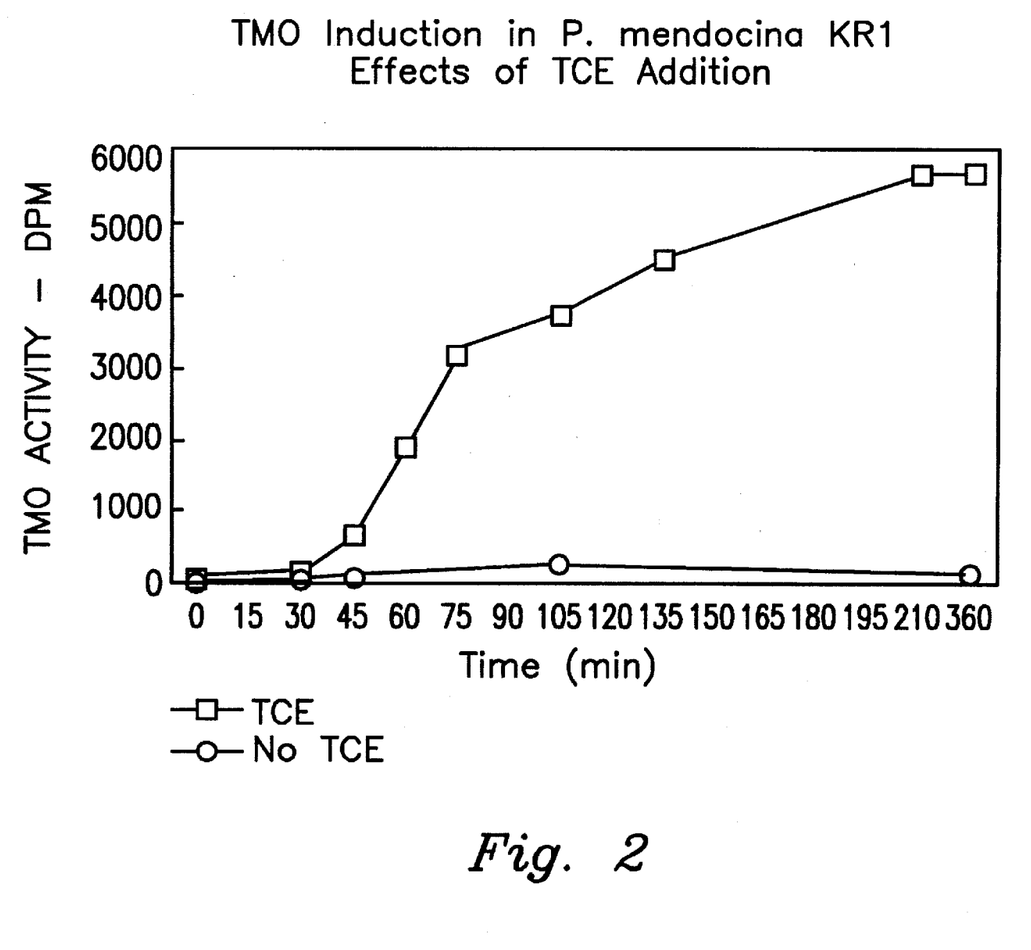
FIG. 2 is a graph showing TMO activity in *Pseudomonas mendocina* KR-1 over six hours time, with and without trichloroethylene.

Results of Examples 1 (c) and (d) of the experiments, shown in FIGS. 1 and 2, clearly demonstrate induction of TMO in *Pseudomonas mendocina* by TCE. FIG. 1 shows induced TMO activity over a 30 minute time period as a result of two separate runs. One run (Example 1 (a)) included the introduction of 40 µM final concentration of TCE, while the other (Example 1 (c)) was conducted in the absence of TCE. TMO activity in the *Pseudomonas mendocina*, measured in disintegrations per minute (DPM), increased dramatically over the 30 minute time period in the case where TCE was added to the medium. TMO activity increased at a substantially two fold rate for a ten minute time interval. In Example 1 (c) where no TCE was added to the medium, TMO activity in the *Pseudomonas mendocina* was virtually zero and remained at a low level throughout the duration of the experiment.

FIG. 2 shows a graph of induced TMO activity in *Pseudomonas mendocina* KR-1 from the pair of runs conducted over a six hour time period. One run, Example 1 (b), was conducted in the presence of 40 µM TCE in the medium, while the other run, Example 1 (d), was conducted in the absence of TCE. TMO activity increased greatly in the TCE containing medium (Example 1 (b)) at an extremely rapid rate for the first 75 minutes, up to over 3,000 DPM. The activity further increased almost two fold over the remaining 4½ to 5 hour experiment time period. In sharp contrast, the sample not containing TCE (Example 1 (d)) showed little, if any, TMO activity over the entire course of the six hour experiment.

EXAMPLE 2

Another set of experiments containing five runs was performed to determine the preferred concentration of TCE used to induce the TMO genes in *P. mendocina* KR-1. TCE degradation was measured by suspending cells in BSM to an $OD_{550}$ of 1.0. 10 mL of cells were added to 50 mL serum vials and 10 µL of TCE in dimethylformamide was added (final TCE concentration: 1–80 µM). Vials were sealed with teflon-lined crimp seals and shaken at 30° C. At timed intervals, 250 µl of sample was removed from each sample by using a syringe. The sample was mixed with 250 µl BSM to generate a final volume of 0.5 mL and $OD_{550}$ of 0.5. $^{14}$C-Toluene assays were then performed on the samples as described previously.

Figure 3:
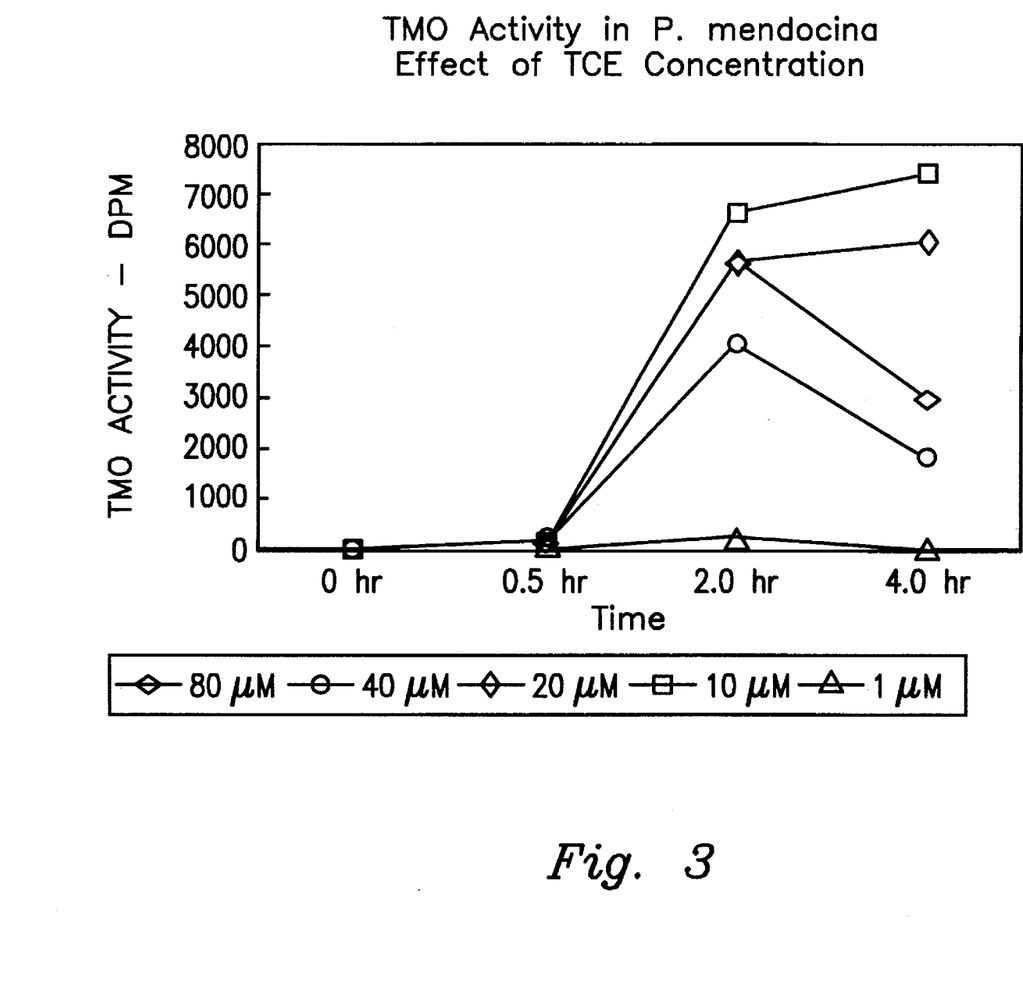
FIG. 3 is a graph showing TMO activity in *Pseudomonas mendocina* over four hours time depending upon concentration of trichloroethylene.

Results of Example 2 and its five runs, shown in FIG. 3, demonstrated that greater than 1 µM of TCE was preferred to induce the TMO genes for degradation of TCE. FIG. 3 shows a graph of TCE induced TMO activity in *Pseudomonas mendocina* KR-1 over a 4 hour test period. The results of the five separate runs are shown in the graph wherein various concentrations of TCE were present. The concentrations included 1, 10, 40 and 80 µM of TCE. In the case where 1 µM TCE was employed, very little TMO activity was measured. However, in the remaining cases where 10 µM or more of TCE were present, TMO activity increased dramatically after the first half hour of the test period. In two cases, the lower concentrations of 10 and 20 µM provided the best results with respect to induction of TMO activity. Higher concentrations were also quite effective. Accordingly, the preferred concentration is 10 µM to 80 µM, most preferably 10 µM to 20 µM.

EXAMPLE 3

The effect of three growth substrates on TCE induced TMO activity was also established through a series of four runs. Cells were grown overnight as previously described for non-inducing growth: 30° C., 100 RPM, 50 mL cells in 125 mL flask in BSM with either 3 g/L sodium glutamate, 20 mM lactate, or 2 g/L glucose. The cultures were then washed and suspended to an $O.D._{550}$=1.0 in BSM plus 0.3 g/L glutamate, 2.0 mM lactate, and 0.2 g/L glucose, respectively. TCE was then added to a final concentration of 40 µM, vials were sealed, and shaken at 30° C. One run contained no TCE as a control. $^{14}$C toluene assays for TMO activity were performed as previously described at timed intervals and the quantity of TCE remaining in the vials was determined by using a TCE bottle assay and gas chromatography. At timed intervals, 10 µL of the air above the reaction mixture was removed from the vials by using a gas-tight syringe, and injected onto a gas chromatograph (Varian 3400; Star Data System) equipped with a 30M VOCOL column (Supelco Inc.: c0.53 mm ID, 1 µL film, helium carrier at 7 mL/min, 100° C. isothermal, injector at 225° C.) and an electron capture detector (GC-ECD; 300° C.) to quantify the TCE remaining in the vial. Relative TCE concentration was enumerated as area counts, greater area counts representing greater amounts of TCE remaining in the vials. Five cell suspensions as described above were supplemented with 1 µM, 10 µM, 20 µM, 40 µM and 80 µM of TCE. A control run not shown in FIG. 3, and performed in the same manner as the other five runs, contained only DMF. Cell suspensions were incubated at 30° C. with shaking, and TMO activity, as described above with respect to Example 1, was determined at timed intervals.

Figure 4:
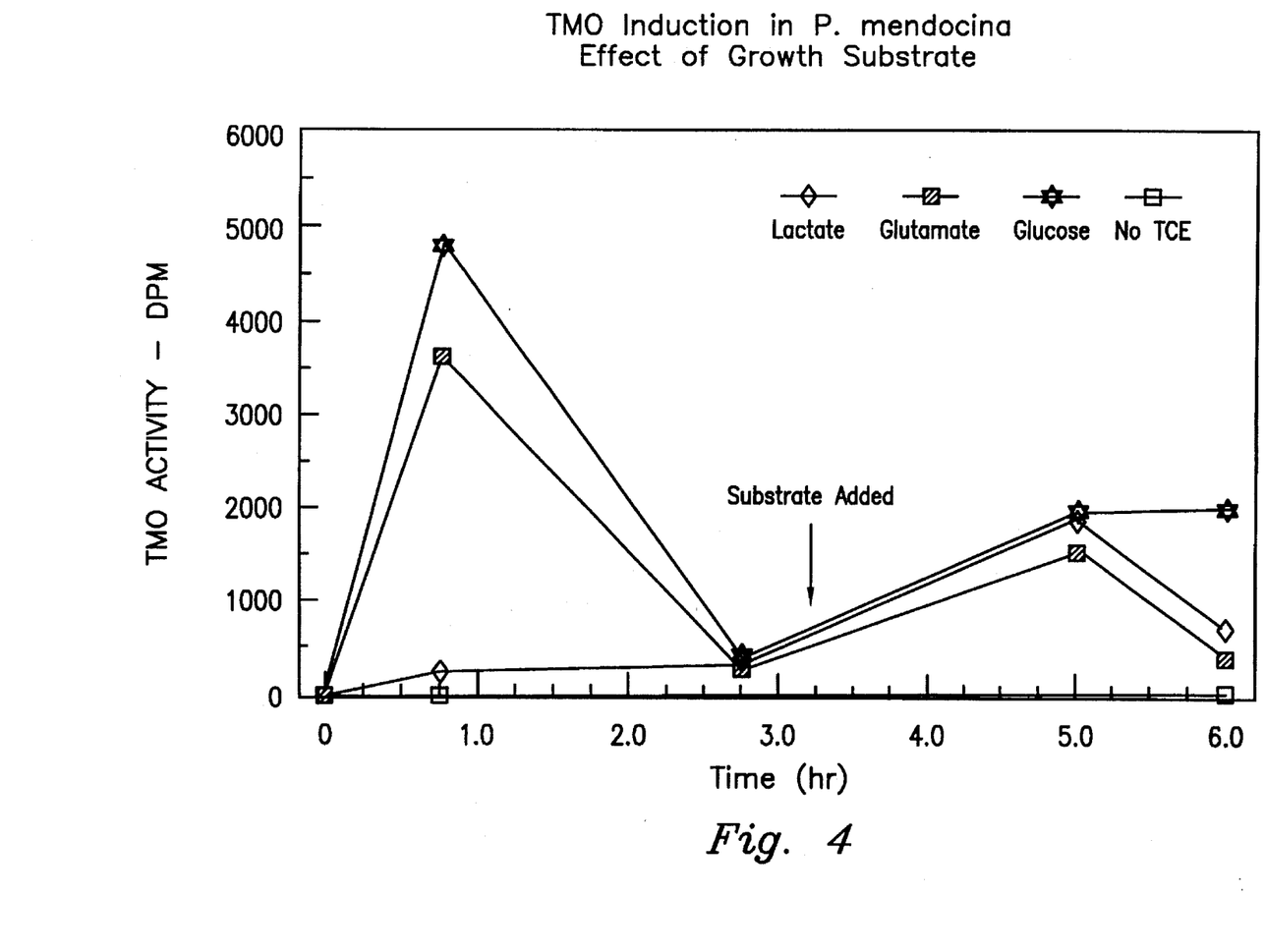
FIG. 4 is a graph showing TMO activity of *Pseudomonas mendocina* over six hours time in conjunction with various growth substrates.
Figure 5:
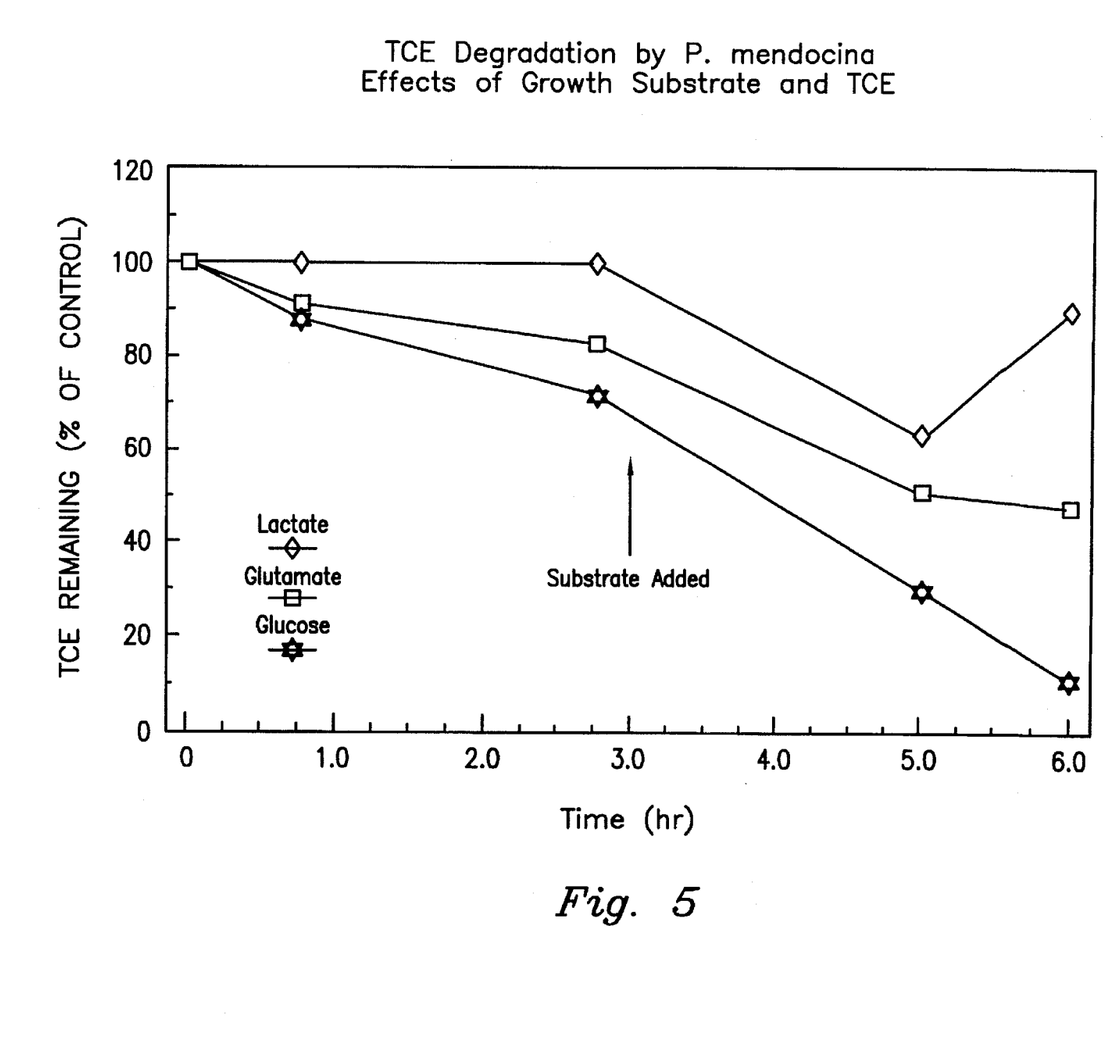
FIG. 5 is a graph showing TCE degradation by *Pseudomonas mendocina* over time and in the presence of different growth substrates.

Results of Example 3, shown in FIGS. 4 and 5, demonstrated rapid induction of glutamate- and glucose-grown cells by TCE. FIG. 4 shows induced TMO activity over a 6 hour time period. Lactate, glutamate and glucose growth substrates are shown in the diamond, solid square and star graph lines representing three runs, while the separate control run containing no TCE is shown by the open square lines. The glutamate and glucose runs showed exceptional TMO activity increases up to 3,500 and just under 5,000 DPM, respectively. FIG. 4 shows that after 2.75 hours, TMO activity in all samples was near zero, the no TCE control sample and the lactate run having produced little or no TMO activity up to that point. Additional carbon substrate (3 g/L glutamate, 2 g/L glucose, or 20 mM lactate) was added and the incubations were continued at 30° C., with shaking. All samples responded to the substrate addition as indicated by an increase in TMO activity, except the no TCE control sample. TMO activity in each case increased by a factor of at least 5 after addition of the substrate (FIG. 4).

FIG. 5 shows TCE degradation by *Pseudomonas mendocina* employing the same samples as described in FIG. 4. Three curves on the graph represent cells grown with, and addition of, lactate, glutamate, glucose and the relative effect on the quantity of TCE remaining over a 6 hour time period. TCE degradation was quantified by measuring the amount of TCE remaining in sealed vials by using the previously described gas chromatographic method. FIG. 5 shows TCE concentrations decreased in response to TMO induction. Of the thee growth substrates evaluated, glucose showed the greatest effect on TCE degradation.

Figure 6:
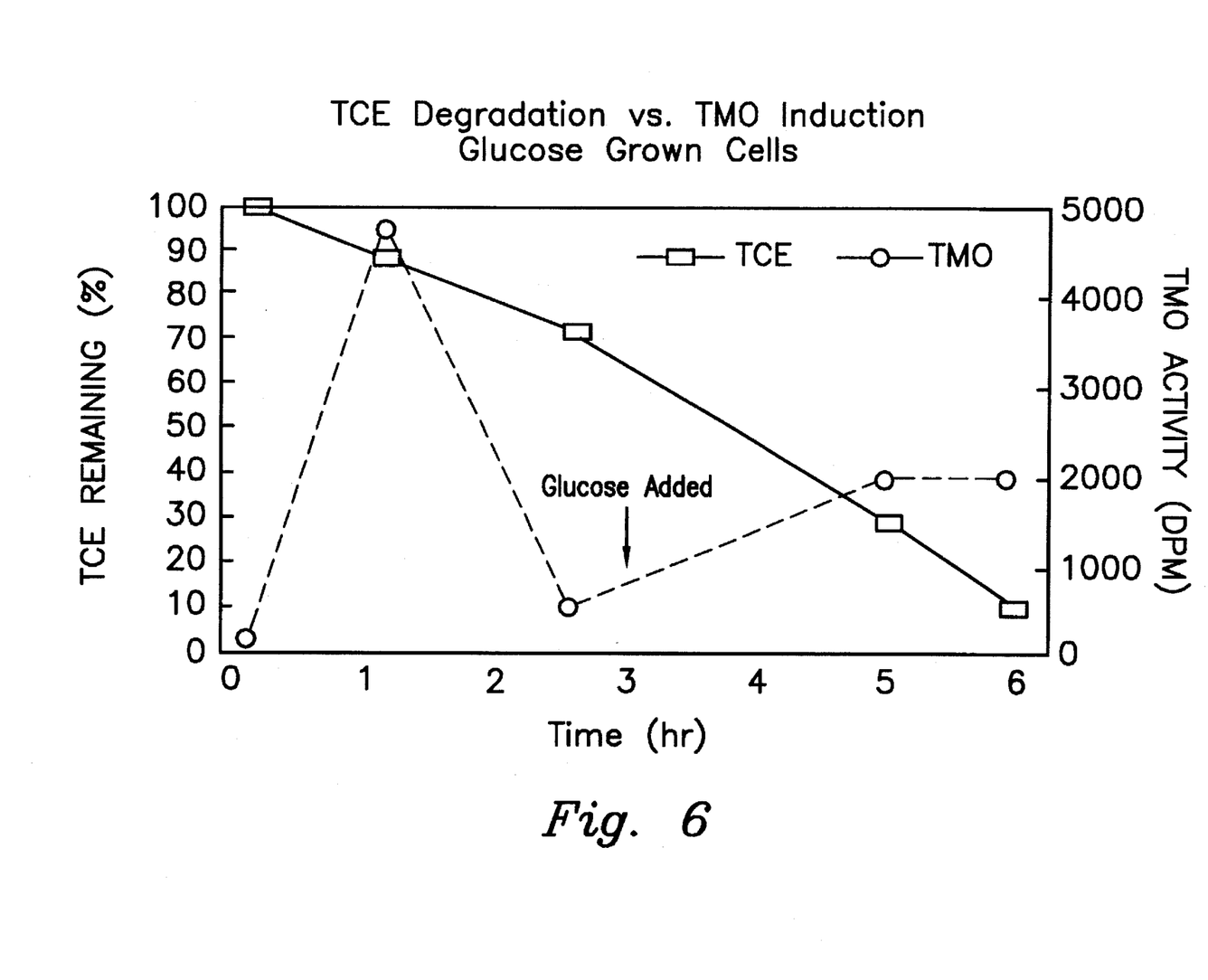
FIG. 6 is a graph of TMO activity over six hours time overlapped with TCE degradation.

FIG. 6 shows a graph of TCE degradation versus TMO induction over a 6 hour time period. The left portion of the graph shows the percentage of TCE remaining, which ranges from 100% down to about 10%, while the right hand side shows corresponding TMO activity. FIG. 6 indicates that TCE degradation occurs simply by contacting *Pseudomonas mendocina* cells with TCE, absent any additional inducing substrates. In FIG. 6, glucose (2 g/L) was added after about 3 hours to further enhance TCE degradation. The experimental results shown in the graph indicate that lengthening the experiment time would reduce TCE quantities even further.

It has also been discovered that alkanes, such as pentane, hexane, octane and decane, for example, can act as a growth substrate for *Pseudomonas mendocina*. This provides great advantages over prior remediation efforts. In many situations multiple contaminants may be found, such as TCE, DCE and other VOC's, together with gasoline or other fuels, which contain large quantities of alkanes. Alkane assisted growth of *Pseudomonas mendocina* KR-1 assists in better degrading TCE and simultaneously consuming the alkanes, thereby creating an enhanced remediation technique in such situations where alkanes are also located. A series of tests as described below resulted in the following results.

EXAMPLE 4

To determine the ability of alkanes to assist in the induction of TMO activity in *P. mendocina* KR-1 and to subsequently degrade TCE, the organism was grown in basal salts medium with hexane, octane and pentane as sole carbon and energy sources. TMO activity was determined by using the $^{14}$C-toluene assay and TCE degradation was measured by using a TCE bottle assay, both as described previously.

*P. mendocina* KR-1 was grown in either BSM+sodium glutamate (3 g/l) or glucose (0.2%) (control), or BSM+ hexane, pentane, octane or toluene supplied as vapor. Cells were grown for 48 hr, washed with BSM, then suspended to an $OD_{550}$ of 1.0 in BSM. Cells were incubated for 1 hr to allow removal of most residual alkane. They were then subjected to TMO and TCE assays. Table 1 shows the result of one such TMO assay.

TABLE 1

| Growth Substrate | TMO Activity (DPM) | % Activity |
|---|---|---|
| Toluene | 17507 | 100 |
| Hexanes | 4889 | 29 |
| Pentane | 2079 | 12 |

TABLE 1-continued

| Growth Substrate | TMO Activity (DPM) | % Activity |
|---|---|---|
| Octane | 3915 | 23 |
| Gultamate | 123 | 0.7 |

TMO activity in alkane-grown cells was from 12 to 29% of that obtained with toluene-grown cells. Actual activities in alkane grown cells can actually be higher than that measured if residual alkanes remained with, in, or attached-to the cells. Residual alkanes could be competitive inhibitors that prevent oxidation of the $^{14}$C-toluene used in the assay.

In another experiment as shown in Table 2, *P. mendocina* was grown in BSM+ sodium glutamate, collected and washed, and suspended to an $OD_{550}$ of 1.0. A TMO assay was performed on the cells. Then 5 ml of the culture was added to each of four 50 mL serum vials. The vials were amended with either 5 μl toluene, 25 μl pentane, 25 μl pentane+100 μl 1M HCl (killed) or no additions. The vials were incubated at 30° C. and sampled, by using a glass syringe, at 1.5 hr and 2.5 hr after substrate addition. The samples were diluted to an $OD_{550}$=0.5 and subjected to a $^{14}$C-toluene assay. Results demonstrate induction of TMO by pentane. It is unclear why only limited activity was observed in toluene amended cultures, but cultures may have been sensitive to the concentrations of toluene used in the experiment.

TABLE 2

| | TMO Activity (DPM) | | |
|---|---|---|---|
| Substrate Added | T = 0 | T = 1.5 hr. | T = 2.5 hr. |
| None | 126 | 160 | 140 |
| Toluene | 126 | 108 | 198 |
| Pentane | 126 | 2480 | 1293 |
| Killed + Pentane | 126 | 128 | 121 |

Figure 7:
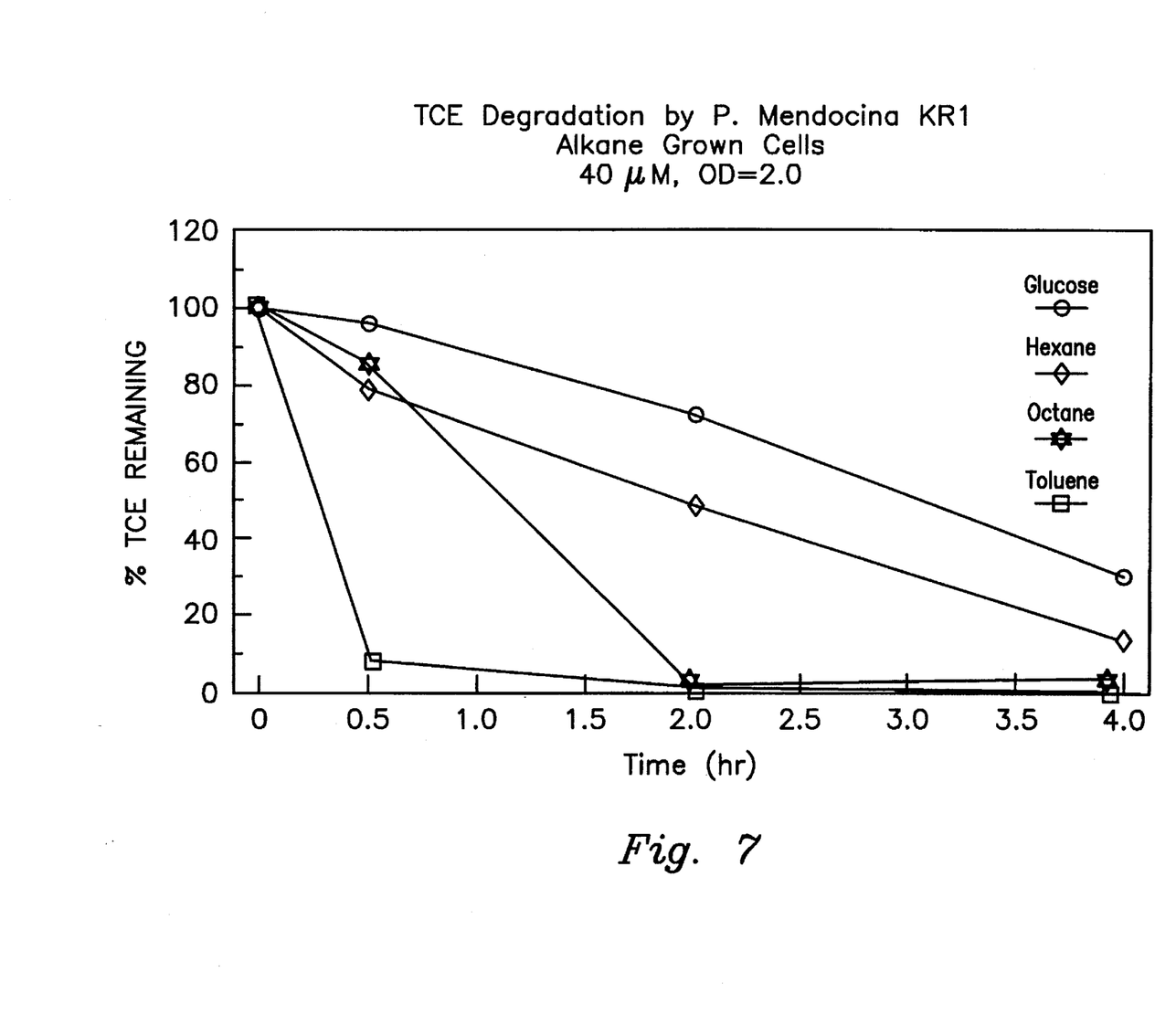
FIG. 7 is a graph of TCE degradation of *Pseudomonas mendocina* over four hours in the presence of different alkane growth substrates.

Finally, alkane grown cells were analyzed for their ability to degrade TCE by using the TCE bottle assay and cells suspended in BSM to $OD_{550}$=2.0. FIG. 7 demonstrates that alkane grown cells degrade TCE. Loss of TCE in the control (glucose) sample is thought to be due to induction of TMO by TCE.

Although the invention has been described with reference to specific forms selected for discussion in the Specification, it will be appreciated that modifications may be made, that certain steps may be performed independently of other steps, and that a wide variety of equivalents may be utilized, all without departing from the spirit and scope of the invention which is defined in the appended claims.

What is claimed is:

1. A method of degrading trichloroethylene in a medium contaminated with a 1 μM or higher concentration of said trichloroethylene, said method comprising the steps of:

(a) introducing a degradation effective mount of *Pseudomonas mendocina* KR-1 ATCC 55706 into said medium under conditions sufficient to degrade said trichloroethylene;

(b) inducing, with said trichloroethylene, toluene monooxygenase genes naturally occurring within said *Pseudomonas mendocina* KR-1 ATCC 55706; and (c) degrading with said *Pseudomonas mendocina* KR-1 ATCC 55706 and with said toluene monooxygenase genes induced by said trichloroethylene at least a portion of said trichloroethylene in said medium.

2. A method of degrading a volatile organochloride comprising:

contacting degradation effective amounts of *Pseudomonas mendocina* KR-1 ATCC 55706 and trichloroethylene with said volatile organochloride; and degrading with said *Pseudomonas mendocina* KR-1 ATCC 55706 said volatile organochloride.

3. The method defined in claim 2 wherein said volatile organochloride is a pollutant located in a contaminated medium and the degradation remediates said medium.

4. The method deemed in claim 2 whereto said volatile organochloride is selected from the group consisting of trichloroethylene, dichloroethylene, vinylchloride and ethylene chloride.

5. The method defined in claim 2 further comprising contacting said *Pseudomonas mendocina* KR-1 ATCC 55706 with a growth substrate before contacting said *Pseudomonas mendocina* KR-1 ATCC 55706 and said trichloroethylene with said volatile organochloride.

6. The method defined in claim 5 wherein said growth substrate is selected from the group consisting of glutamate, lactate, glucose and alkanes.

7. The method defined in claim 5 wherein said growth substrate is selected from the group consisting of pentune, hexane, octane and decane.

8. The method defined in claim 2 wherein said volatile organochloride is trichloroethylene.

9. The method defined in claim 8 wherein said trichloroethylene is a pollutant located in a contaminated media and the degradation remediates said media.

10. A method of degrading trichlorethylene comprising:

contacting trichloroethylene with a degradation effective mount of *Pseudomonas mendocina* KR-1 ATCC 55706; and catalyzing a degradation of said trichloroethylene by induction of toluene monooxygenase genes naturally occurring within said *Pseudomonas mendocina* KR-1 ATCC 55706 with said trichloroethylene.

11. The method defined in claim 10 wherein a 1 µM or higher concentration of said trichloroethylene induces said toluene monooxygenase genes.

12. The method defined in claim 10 further comprising contacting said *Pseudomonas mendocina* KR-1 ATCC 55706 with a growth substrate before contacting said trichloroethylene with said *Pseudomonas mendocina* KR-1 ATCC 55706.

13. The method defined in claim 12 wherein said growth substrate is selected from the group consisting of glummate, lactate, glucose and alkanes.

14. The method defined in claim 12 wherein said growth substrate is selected from the group consisting of penlane, hexane. octane and decane.

15. A method of remediating a medium contaminated with at least one volatile organochloride comprising:

contacting said at least one volatile organochloride with a degradation effective amount of *Pseudomonas mendocina* KR-1 ATCC 55706; and degrading with said *Pseudomonas mendocina* KR-1 ATCC 55706 said at least one volatile organochloride by contacting said *Pseudomonas mendocina* KR-1 with a degradation effective mount of trichloroethylene.

16. The method defined in claim 15 wherein said medium is selected from the group consisting of ground water, waste water, soil, sludges, sediments, drinking water, leachates and chemical waste.

17. The method defined in claim 15 wherein said at least one volatile organochloride includes said trichloroethylene.

18. The method defined in claim 15 further comprising contacting said *Pseudomonas mendocina* KR-1 ATCC 55706 with a growth substrate before degrading with said *Pseudomonas mendocina* KR-1 ATCC 55706 said at least one volatile organochloride.

19. The method defined in claim 18 wherein said growth substrate is selected from the group consisting of glutamate, lactate, glucose, penlane, hexane, octane and decane.

20. The method defined in claim 15 wherein the step of degrading results from induction of toluene monooxygenase genes naturally occurring within said *Pseudomonas mendocina* KR-1 by said trichloroethylene.

21. The method defined in claim 20 wherein a 1 µM or higher concentration of said trichloroethylene induces said toluene monooxygenase genes.

* * * * *